United States Patent
Sems et al.

(10) Patent No.: US 10,456,177 B2
(45) Date of Patent: Oct. 29, 2019

(54) INTRAMEDULLARY DEVICE WITH COMPOUND FASTENER TRAJECTORIES

(71) Applicant: Biomet C.V., Warsaw, IN (US)

(72) Inventors: Stephen Andrew Sems, Rochester, MN (US); Daniel S Horwitz, Danville, PA (US); Tracy J. Watson, Town & Country, MO (US); Michael Karl-Heinz Wich, Berlin (DE); Greg Gohring, Wabash, IN (US); Daren David Granger, Warsaw, IN (US); Joseph Michael O'Reilly, Granger, IN (US)

(73) Assignee: Biomet C.V., Warsaw, IN (US)

( * ) Notice: Subject to any disclaimer, the term of this patent is extended or adjusted under 35 U.S.C. 154(b) by 0 days.

(21) Appl. No.: 15/837,019

(22) Filed: Dec. 11, 2017

(65) Prior Publication Data

US 2018/0193067 A1    Jul. 12, 2018

Related U.S. Application Data

(63) Continuation of application No. 14/568,535, filed on Dec. 12, 2014, now Pat. No. 9,839,454.

(Continued)

(51) Int. Cl.
*A61B 17/72*    (2006.01)

(52) U.S. Cl.
CPC .......... *A61B 17/7233* (2013.01); *A61B 17/72* (2013.01)

(58) Field of Classification Search
CPC ............................ A61B 17/72; A61B 17/7233

(Continued)

(56) References Cited

U.S. PATENT DOCUMENTS 4,622,959 A * 11/1986 Marcus .............. A61B 17/1721
  606/64
5,549,610 A *  8/1996 Russell .................. A61B 17/72
  606/62

(Continued)

FOREIGN PATENT DOCUMENTS

CN        106456219 A      2/2017
JP       2012531955 A     12/2012

(Continued)

OTHER PUBLICATIONS

"U.S. Appl. No. 14/568,535, Final Office Action dated Apr. 20, 2017", 6 pgs.

(Continued)

*Primary Examiner* — Pedro Philogene
*Assistant Examiner* — David C Comstock
(74) *Attorney, Agent, or Firm* — Schwegman Lundberg & Woessner, P.A.

(57) ABSTRACT

An intramedullary device, having a first longitudinal axis extending between a proximal end and a distal end thereof, is provided. The intramedullary device may include a first bore and a second bore. The first bore may include a second longitudinal axis and may extend through the intramedullary device between a first opening and a second opening. The second longitudinal axis may define a first angle (θ1) with the first longitudinal axis. The second bore may include a third longitudinal axis and may extend through the intramedullary device between the first opening and a third opening. The third longitudinal axis may define a second angle (θ2) with the first longitudinal axis.

20 Claims, 4 Drawing Sheets

Related U.S. Application Data

(60) Provisional application No. 61/968,636, filed on Mar. 21, 2014.

(58) Field of Classification Search
  USPC ..................................................... 606/62, 64
  See application file for complete search history.

(56) References Cited

U.S. PATENT DOCUMENTS

| | | | |
|---|---|---|---|
| 5,658,288 | A | 8/1997 | Kim |
| 5,713,902 | A | 2/1998 | Friedl |
| 8,157,803 | B1 | 4/2012 | Zirkle, Jr. et al. |
| 9,839,454 | B2 | 12/2017 | Sems et al. |
| 2003/0069581 | A1* | 4/2003 | Stinson ............... A61B 17/921 606/62 |
| 2004/0172026 | A1 | 9/2004 | Ekholm et al. |
| 2005/0055023 | A1 | 3/2005 | Sohngen et al. |
| 2006/0111716 | A1 | 5/2006 | Schlienger et al. |
| 2006/0149257 | A1 | 7/2006 | Orbay et al. |
| 2007/0123878 | A1* | 5/2007 | Shaver ................ A61B 17/72 606/64 |
| 2008/0009869 | A1* | 1/2008 | Schlienger ........... A61B 17/72 606/64 |
| 2008/0294164 | A1* | 11/2008 | Frank ................ A61B 17/7233 606/64 |
| 2009/0149861 | A1 | 6/2009 | Brodsky et al. |
| 2011/0282347 | A1 | 11/2011 | Gordon et al. |
| 2012/0143192 | A1 | 6/2012 | Watanabe et al. |
| 2012/0197255 | A1* | 8/2012 | Elghazaly ........... A61B 17/725 606/64 |
| 2015/0265323 | A1 | 9/2015 | Sems et al. |

FOREIGN PATENT DOCUMENTS

| | | |
|---|---|---|
| JP | 2017509461 A | 4/2017 |
| WO | WO-9613220 A1 | 5/1996 |
| WO | WO-2015143112 A1 | 9/2015 |

OTHER PUBLICATIONS

"U.S. Appl. No. 14/568,535, Non Final Office Action dated Aug. 26, 2016", 6 pgs.

"U.S. Appl. No. 14/568,535, Notice of Allowance dated Aug. 11, 2017", 5 pgs.

"U.S. Appl. No. 14/568,535, Response filed Jul. 20, 2017 to Non Final Office Action dated Apr. 20, 2017", 11 pgs.

"U.S. Appl. No. 14/568,535, Response filed Dec. 16, 2016 to Non Final Office Action dated Aug. 26, 2016", 9 pgs.

"International Application Serial No. PCT/US2015/021393, International Preliminary Report on Patentability dated Sep. 29, 2016", 8 pgs.

"International Application Serial No. PCT/US2015/021393, International Search Report dated Jul. 8, 2015", 3 pgs.

"International Application Serial No. PCT/US2015/021393, Written Opinion dated Jul. 8, 2015", 7 pgs.

"Australian Application Serial No. 2015231245, First Examination Report dated Sep. 20, 2018", 2 pgs.

"Chinese Application Serial No. 201580021694.X, Office Action dated Jun. 5, 2018", w/ English translation, 5 pgs.

"Canadian Application Serial No. 2,943,161, Office Action dated Sep. 27, 2018", 3 pgs.

"Chinese Application Serial No. 201580021694.X, Response filed Oct. 17, 2018 to Office Action dated Jun. 5, 2018", w/o English claims or translation, 3 pgs.

"European Application Serial No. 15721362.0, Communication Pursuant to Article 94(3) EPC dated Nov. 9, 2018", 4 pgs.

"European Application Serial No. 15721362.0, Response Filed Feb. 19, 2019 Communication Pursuant to Article 94(3) EPC dated Nov. 9, 2018", 11 pgs.

"Japanese Application Serial No. 2017-501105, Notification of Reasons for Refusal dated Jan. 29, 2019", 14 pgs.

"Chinese Application Serial No. 201580021694.X, Office Action dated Mar. 25, 2019", w/ English translation, 18 pgs.

"Chinese Applicaiton Serial No. 201580021694.X, Response filed Jun. 5, 2019 to Office Action dated Mar. 25, 2019", w/English claims.

"Japanese Application Serial No. 2017-501105, Response filed Jul. 29, 2019 to Notification of Reasons for Refusal dated Jan. 29, 2019", w/ English claims, 9 pgs.

\* cited by examiner

INTRAMEDULLARY DEVICE WITH COMPOUND FASTENER TRAJECTORIES

CROSS-REFERENCE TO RELATED APPLICATIONS

This application claims the benefit of U.S. Provisional Application No. 61/968,636, filed on Mar. 21, 2014. The entire disclosure of the above application is incorporated herein by reference.

FIELD

The present disclosure relates to an intramedullary device, and more particularly to an intramedullary fixation device with compound trajectories.

BACKGROUND

This section provides background information related to the present disclosure which is not necessarily prior art.

Various types of surgical procedures may require the use of an intramedullary fixation device, such as a rod or pin, to anchor or interconnect a first portion of a bone to a second portion of the bone. Intramedullary fixation devices may include a cannulated or non-cannulated tubular body. The tubular body may include a plurality of through-bores disposed at various angles relative to each other, in order to obtain angular stability, improve retention within the bone, and optimize the placement of the intramedullary fixation device within the bone. Screws, or other bone fixation devices, may be placed within the through-bores to secure the intramedullary fixation device within the bone.

While known intramedullary fixation devices have proven to be acceptable for their intended purposes, a continued need for improvement in the art remains.

SUMMARY

This section provides a general summary of the disclosure, and is not a comprehensive disclosure of its full scope or all of its features.

According to one particular aspect, the present disclosure provides an intramedullary device. The intramedullary device may have a first longitudinal axis extending between a proximal end and a distal end thereof. The intramedullary device may further include a first bore and a second bore. The first bore may include a second longitudinal axis and may extend through the intramedullary device between a first opening and a second opening. The second longitudinal axis may define a first angle with the first longitudinal axis. The second bore may include a third longitudinal axis and may extend through the intramedullary device between the first opening and a third opening. The third longitudinal axis may define a second angle with the first longitudinal axis.

According to another particular aspect, the present disclosure provides an intramedullary device defining a first longitudinal axis extending between a proximal end and a distal end thereof. The intramedullary device may include a first bore, a second bore, a third bore, and a fourth bore. The first bore may have a second longitudinal axis extending in a direction substantially perpendicular to the first longitudinal axis. The second bore may have a third longitudinal axis extending in a direction substantially perpendicular to the first and second longitudinal axes. The third bore may have a fourth longitudinal axis that defines a first angle with the second and third longitudinal axes. The third bore may extend between a first opening and a second opening. The fourth bore may have a fifth longitudinal axis that defines a second angle with the second and third longitudinal axes. The fourth bore may extend between the first opening and a third opening. The first opening may define a perimeter and include a first lobe portion and a second lobe portion.

According to yet another particular aspect, the present disclosure provides an intramedullary device defining a first longitudinal axis extending between a proximal end and a distal end thereof. The intramedullary device may include a first region and a second region. The first region may include a first bore and a second bore. The first bore may have a second longitudinal axis that defines a first angle with the first longitudinal axis. The first bore may extend through the intramedullary device between a first opening and a second opening. The second bore may have a third longitudinal axis that defines a second angle with the first longitudinal axis. The second bore may extend through the intramedullary device between the first opening and a third opening. The second region may include a third bore and a fourth bore. The third bore may have a fourth longitudinal axis and may extend between a fourth opening and a fifth opening. The fourth bore may have a fifth longitudinal axis that defines a third angle with the fourth longitudinal axis. The fourth bore may extend between the fourth opening and a sixth opening.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
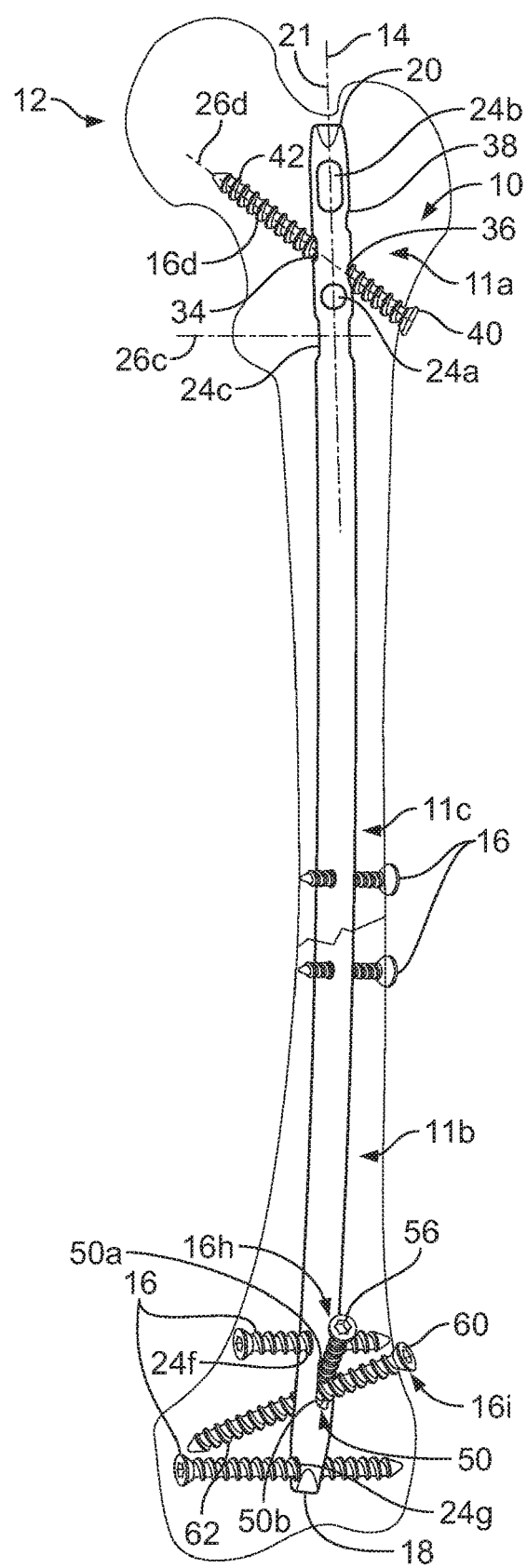
FIG. 1 is an environmental view illustrating an intramedullary device in accordance with the principles of the present disclosure, the intramedullary device shown operatively implanted within a femur.

Example embodiments will now be described more fully with reference to the accompanying drawings.

With reference to FIGS. 1-4, an intramedullary device constructed in accordance with the principles of the present disclosure is illustrated and identified at reference character 10. The intramedullary device 10 may be inserted into a bone 12, generally along a longitudinal axis 14 thereof. The device 10 may be fixed to or otherwise secured within the bone 12 using a plurality of fasteners 16, such as bone screws, nails, or other suitable mechanical fastening devices. According to one exemplary use, the device 10 may be inserted into a femur or a tibia from a knee joint, and upward toward a hip or downward toward an ankle, respectively. It will also be appreciated, however, that the intramedullary device 10 may be adapted for insertion into other bones and/or tissues, and similarly inserted from different ends of the bones.

Figure 2A:
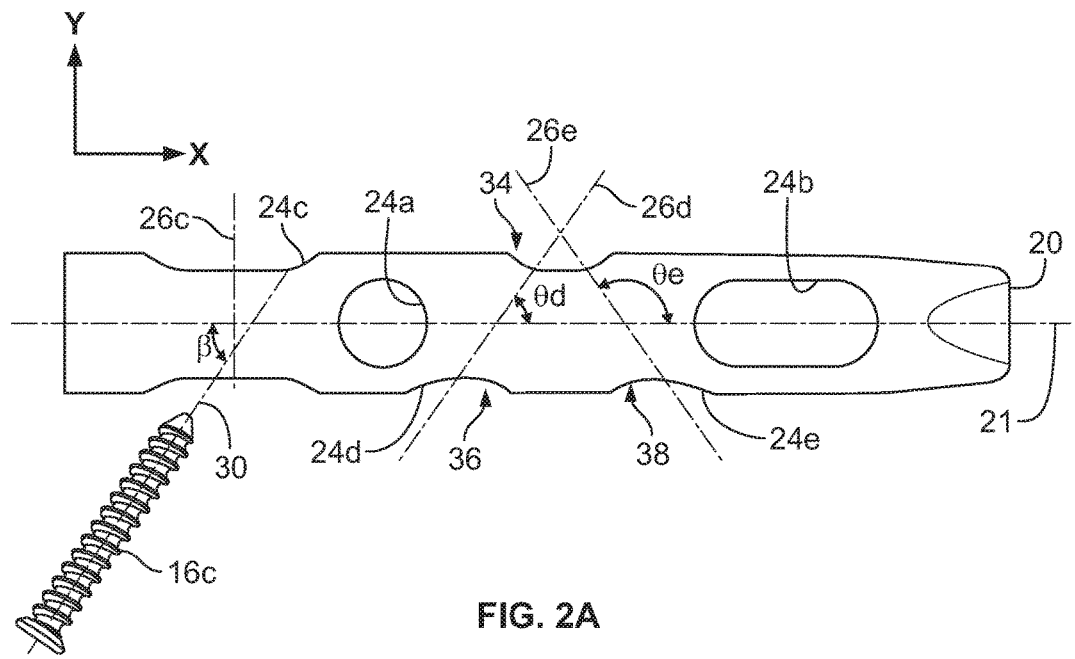
FIG. 2A is a side view of a first end of the intramedullary device of FIG. 1.
Figure 4:
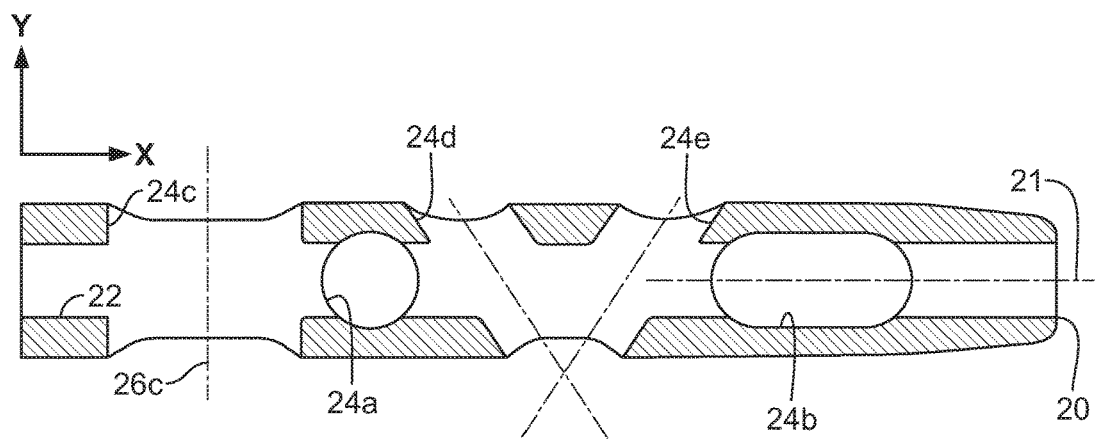
FIG. 4 is a cross-sectional view of a first end of the intramedullary device of FIG. 1, taken through the line 4-4 of FIG. 3.

The intramedullary device 10 may be a rod-like member having a substantially cylindrical construct extending from a proximal end 18 to a distal end 20 along a longitudinal axis 21. In one configuration, the proximal end 18 may be a driving end. In this regard, a force may be applied to the proximal end 18 of the device 10, via a hammer, mallet, or other suitable driving apparatus (not shown), for securing the device 10 within the bone 12. In other configurations, the distal end 20 may be a driving end. As illustrated in FIG. 2A, the longitudinal axis 21 may extend in a direction substantially parallel to the X-axis. In an assembled configuration, the longitudinal axis 21 of the device 10 may be substantially aligned with the longitudinal axis 14 of the bone 12. As illustrated in FIG. 4, in one configuration the intramedullary device 10 may include a cylindrical cavity 22 extending between the proximal end 18 and the distal end 20 along the longitudinal axis 21, such that the device 10 defines a generally cannulated construct along a substantial portion or an entirety of the device. It will also be appreciated that in other configurations, the intramedullary device 10, or portions thereof, may be a substantially solid construct.

The device 10 may include a plurality of bores 24 disposed at multiple or compound angles and/or trajectories in a first region 11a of the device 10. In one configuration, the device 10 may include a first bore 24a, a second bore 24b, a third bore 24c, a fourth bore 24d, and a fifth bore 24e. The bores 24a-24e may be disposed generally in the distal end 20 of the device 10. At least one of the bores 24a-24e may be a threaded bore, operable to receive and mate with a threaded fastener. As will be explained in more detail below, the cavity 22 and the first through fifth bores 24a-24e may be disposed in the intramedullary device 10 such that the cavity 22 is in communication with, or otherwise opens into, each of the bores 24a-24e.

Figure 3:
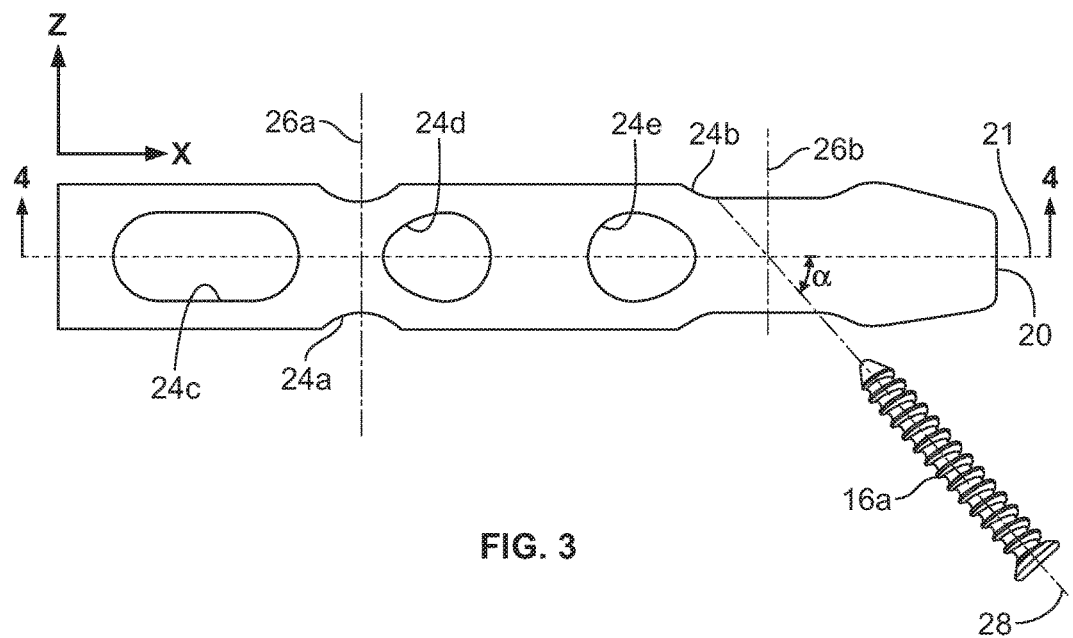
FIG. 3 is a top view of a first end of the intramedullary device of FIG. 1.

As illustrated in FIG. 3, the first and second bores 24a, 24b may define longitudinal axes 26a, 26b, respectively. The first and second bores 24a, 24b may extend radially through the device 10 such that the longitudinal axes 26a, 26b are substantially perpendicular to the longitudinal axis 21 of the device 10, and generally parallel to the Z-axis. In one configuration, the first bore 24a includes a substantially circular cross section, and the second bore 24b includes an oblong or oval cross section. The oblong or oval cross section of the second bore 24b allows the user to vary an angle α formed by the longitudinal axis 21 of the device 10 and a longitudinal axis 28 of the fastener 16a. The oblong or oval cross section of the second bore 24b also allows the user to vary a distance between the fastener 16a and the distal end 20 of the device 10. It will also be appreciated that the cross-sectional area of the first and second bores 24a, 24b may include other shapes within the scope of the present disclosure.

The third bore 24c may define a longitudinal axis 26c. The third bore 24c may extend through the device 10 such that the axis 26c is substantially perpendicular to the longitudinal axis 21 of the device 10, and substantially perpendicular to the longitudinal axes 26a, 26b of the first and second bores 24a, 24b, respectively. In this regard, it will be appreciated that the axis 26c may extend in a direction generally parallel to the Y-axis, as illustrated in FIG. 2A. In one configuration, the third bore 24c includes an oblong or oval cross section. The oblong or oval cross section of the third bore 24c allows the user to vary an angle β formed by the longitudinal axis 21 of the device 10 and a longitudinal axis 30 of the fastener 16c. The oblong or oval cross section of the third bore 24c also allows the user to vary a distance between the fastener 16c and the distal end 20 of the device 10. It will also be appreciated that the cross-sectional area of the third bore 24c may include other shapes within the scope of the present disclosure.

Figure 2B:
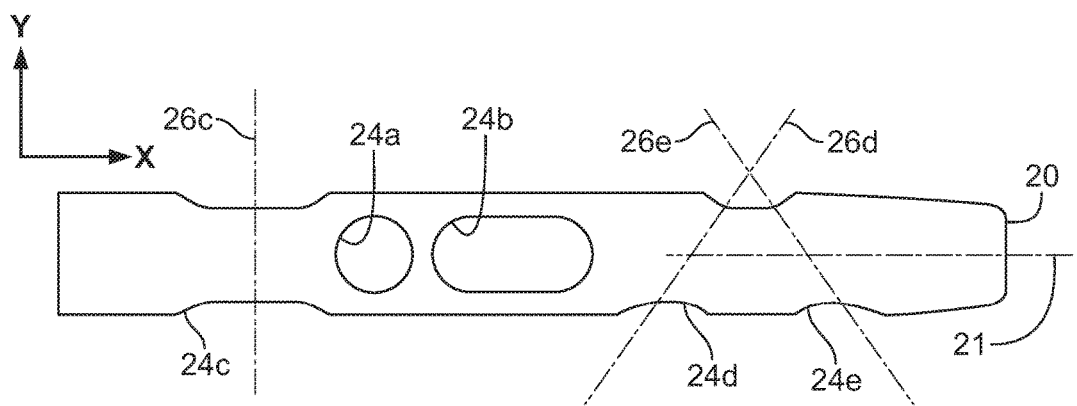
FIG. 2B is a side view of another configuration of a first end of the intramedullary device of FIG. 1.

In one configuration, the fourth and fifth bores 24d, 24e may be located between the second and third bores 24b, 24c (FIG. 2A). In another configuration, the fourth and fifth bores 24d, 24e may be located between the second bore 24c and the distal end 20 of the intramedullary device 10 (FIG. 2B). In other configurations, the fourth and fifth bores 24d, 24e may be located in other positions with respect to the first, second and third bores 24a-24c.

The fourth and fifth bores 24d, 24e may define longitudinal axes 26d, 26e, respectively. The fourth and fifth bores 24d, 24e may extend through the device 10 such that the longitudinal axes 26d, 26e are substantially perpendicular to the X-Z plane. In this regard, the fourth and fifth bores 24d, 24e may extend in the X-Y plane. As illustrated in FIG. 2A, the axes 26d, 26e may form angles θd, θe, respectively, relative to the longitudinal axis 21 of the device 10. The angle θd may be between forty degrees and sixty degrees. The angle θe may be between one hundred twenty degrees and one hundred sixty degrees. In one configuration, the angle θd may be substantially equal to forty-five degrees (45°) and the angle θe may be substantially equal to one hundred thirty-five degrees (135°).

The fourth and fifth bores 24d, 24e may extend through the device such that the fourth bore 24d includes a first opening 34 and a second opening 36, and the fifth bore 24e includes the first opening 34 and a third opening 38. As illustrated in FIG. 1, in one configuration a fastener 16d may be inserted through the fourth bore 24d such that a head 40 of the fastener 16d is disposed at, or extends from, the second opening 36 and a stem 42 of the fastener 16d extends from the first opening 34. Likewise, the fastener 16d may be inserted through the fifth bore 24e such that the head 40 of the fastener 16d is disposed at, or extends from, the third opening 38 and the stem 42 of the fastener 16d extends from the first opening 34. In other configurations, the fastener 16d may be disposed within the fourth or fifth bores 24d, 24e, respectively, such that the head 40 of the fastener 16d is disposed at, or extends from, the first opening 34, and the stem 42 of the fastener 16d extends from the second opening or third opening 36, 38. Accordingly, it will be appreciated that the configuration of the bores 24d, 24e, including the first opening 34 and the angles θd, θe, may improve the interchangeability of the intramedullary device 10 with respect to multiple bones 12 (e.g., a left femur and a right femur). It will also be appreciated that the configuration of the fourth and fifth bores 24d, 24e, including the first opening 34 and the angles θd, θe, can allow for fewer openings or holes in the intramedullary device 10, and can thus improve the strength and integrity of the intramedullary device 10.

As shown in FIG. 2A, the first opening 34 may have a substantially circular or oval shape. It will be appreciated, however, that the first opening 34 may have other shapes, including a figure eight shape, within the scope of the present disclosure.

Figure 5:
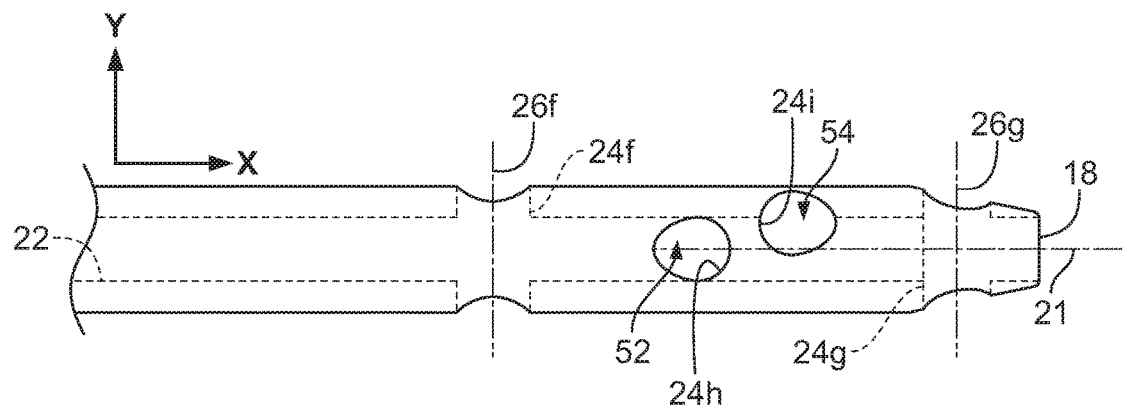
FIG. 5 is a side view of a second end of the intramedullary device of FIG. 1.
Figure 6:
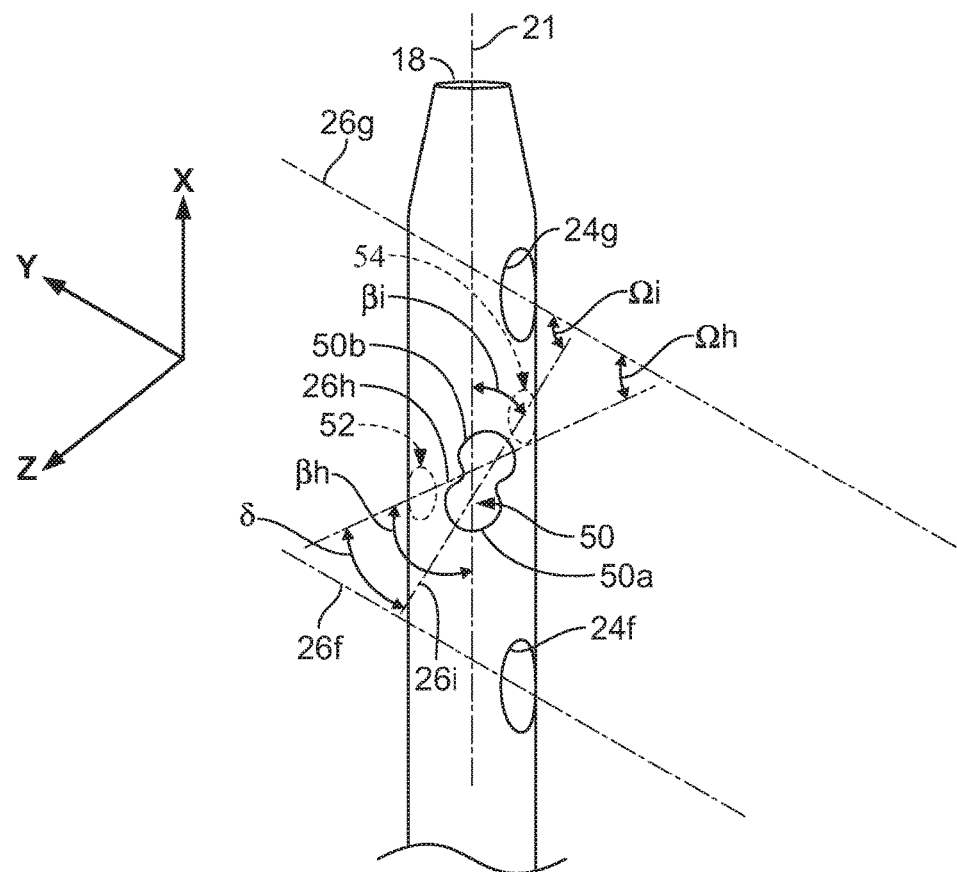
FIG. 6 is a perspective view of a second end of the intramedullary device of FIG. 1.

With reference to FIGS. 5 and 6, the intramedullary device 10 may also include a sixth bore 24f, a seventh bore 24g, an eighth bore 24h, and a ninth bore 24i. The bores 24f-24i may be disposed in a second region 11b of the device 10, generally opposite the first region 11a of the device. In this regard, the first region 11a may include the distal end 20 and the second region 11b may include the proximal end 18. A mid region 11c may extend from and between the first and second regions 11a, 11b, and may include one or more additional fasteners 16.

In one configuration, at least one of the bores 24f-24i may be a threaded bore, operable to receive and mate with a threaded fastener. It will be appreciated that, while the first through ninth bores 24a-24i are generally shown and described as being disposed in the intramedullary device 10, the intramedullary devices 10 may include any combination of the first through ninth bores 24a-24i. As will be explained in more detail below, the cylindrical cavity 22 and the sixth through ninth bores 24f-24i may be disposed in the intramedullary device 10 such that the cylindrical cavity 22 is in communication with, or otherwise opens into, each of the bores 24f-24i.

The sixth and seventh bores 24f, 24g may define longitudinal axes 26f, 26g, respectively. The sixth and seventh bores 24f, 24g may extend through the device 10 such that the longitudinal axes 26f, 26g are substantially perpendicular to the longitudinal axis 21 of the device 10, and generally parallel to the Y-axis, as illustrated in FIG. 5. In this regard, the longitudinal axes 26f, 26g may be oriented in the X-Y plane. As illustrated, in one configuration the sixth and seventh bores 24f, 24g may include a substantially circular cross section. It will be appreciated, however, that the sixth and seventh bores 24f, 24g may include other cross sections (e.g., an oblong or oval cross section) within the scope of the present disclosure.

As illustrated in FIG. 5, in one configuration, the eighth and ninth bores 24h, 24i may be located between the sixth and seventh bores 24f, 24g. In another configuration, the eighth and ninth bores 24h, 24i may be located between the seventh bore 24g and the distal end 20 of the intramedullary device 10. In other configurations, the eighth and ninth bores 24h, 24i may be located in other positions with respect to the sixth and seventh bores 24f, 24g.

The eighth and ninth bores 24h, 24i may define longitudinal axes 26h, 26i, respectively. The eighth and ninth bores 24h, 24i may extend through the device 10 such that the longitudinal axes 26h, 26i define an angle δ therebetween, and further define angles Ωh, Ωi, respectively, relative to the X-Y plane. The angle δ may be between fifteen degrees and seventy-five degrees. In one configuration, the angle δ may be substantially equal to forty-five degrees. The angles Ωh, Ωi may be between five degrees and forty degrees. In one configuration, the angle Ωh may be substantially equal to ten degrees and the angle Ωi may be substantially equal to eighty degrees. In this regard, it will be appreciated that the longitudinal axes 26h, 26i may be non-coplanar.

The eighth and ninth axes 24h, 24i may also define angles βh, βi, respectively, relative to the longitudinal axis 21 of the device. The angles βh, βi may be between fifteen degrees and seventy-five degrees. In one configuration the angles βh, βi may be substantially equal to forty-five degrees. The configuration of the angles Ωh, Ωi and βh, βi may be such that the eighth bore 24h includes a first opening 50 and a second opening 52, and the ninth bore 24i includes the first opening 50 and a third opening 54. As shown in FIG. 6, the first opening 50 may have a substantially "8"-shaped profile. For example, the first opening 50 may define a perimeter including a first lobe portion 50a and a second lobe portion 50b that collectively form a figure eight shape. The first and second lobe portions 50a, 50b may each define substantially circular or oval portions, depending on the desired angles for the fasteners 16.

As illustrated in FIG. 1, in one configuration, a fastener 16h may be inserted through the eighth bore 24h such that a head 56 of the fastener 16h is disposed at, or extends from, the first lobe 50a of the first opening 50, and a stem (not shown) of the fastener 16h extends from the second opening 52. Likewise, a fastener 16i may be inserted through the ninth bore 24i such that a head 60 of the fastener 16i is disposed at, or extends from, the second lobe 50b of the first opening 50, and a stem 62 of the fastener 16i extends from the third opening 54. In other configurations, the fasteners 16h and 16i may be disposed within the eighth and ninth bores 24h, 24i, respectively, such that the head 56 of the fastener 16h is disposed at, or extends from, the second opening 52 and/or the head 60 of the fastener 16i is disposed at, or extends from, the third opening 54. Accordingly, it will be appreciated that the configuration of the bores 24h, 24i, including the first opening 50 and the angles Ωh, Ωi and βh, βi, may improve the interchangeability of the intramedullary device 10 with respect to multiple bones (e.g., a left tibia and a right tibia).

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method, comprising:
    providing an intramedullary device including a first longitudinal axis extending between a proximal end and a distal end thereof, the intramedullary device comprising:
        a proximal region, a distal region, and a mid region positioned between the proximal region and the distal region;
        a first bore extending through the intramedullary device between a first opening and a second opening;
        a second bore extending through the intramedullary device between the first opening and a third opening; and
        a third bore defined by the mid region of the intramedullary device;
    inserting the intramedullary device into a femur in a proximal direction from a knee joint; and
    inserting a first fastener through the third bore, wherein the first bore is configured to receive a second fastener and the third bore is configured to receive a third fastener, such that the second and third fasteners can extend through the intramedullary device concurrently.

2. The method of claim 1, wherein inserting the first fastener comprises inserting the first fastener transverse to the longitudinal axis of the intramedullary device.

3. The method of claim 2, further comprising:
    inserting a third fastener through the distal region of the intramedullary device.

4. The method of claim 3, further comprising:
    inserting a fourth fastener through the distal region of the intramedullary device.

5. The method of claim 4, wherein inserting the third and fourth fasteners comprises:
    inserting the third fastener into the first opening and out of the second opening; and
    inserting the fourth fastener into the first opening and out of the third opening.

6. The method of claim 5, wherein inserting the third and fourth fasteners comprises inserting the third and fourth fasteners such that they extend through the intramedullary device concurrently.

7. The method of claim 4, wherein inserting the third and fourth fasteners comprises inserting the third and fourth fasteners such that:
    the third fastener extends transverse to the longitudinal axis of the intramedullary device;
    the fourth fastener extends transverse to the longitudinal axis of the intramedullary device; and
    the third fastener is non-parallel to the fourth fastener.

8. The method of claim 2, further comprising:
    inserting a third fastener through the proximal region of the intramedullary device.

9. The method of claim 8, wherein inserting the third fastener comprises inserting the third fastener from a lateral side of the intramedullary device to a medial side of the intramedullary device, such that the fastener extends distal to proximal.

10. The method of claim 8, wherein inserting the third fastener comprises inserting the third fastener from a lateral side of the intramedullary device to a medial side of the intramedullary device, such that the fastener extends proximal to distal.

11. The method of claim 1, further comprising:
    inserting a second fastener through a fourth bore defined by the mid region of the intramedullary device.

12. The method of claim 11, wherein inserting the second fastener comprises inserting the second fastener transverse to the longitudinal axis of the intramedullary device.

13. The method of claim 11, wherein inserting the first and second fasteners comprises inserting the first and second fasteners such that the first and second fasteners are substantially parallel.

14. The method of claim 1, wherein inserting the first fastener comprises inserting the first fastener from a lateral side of the intramedullary device to a medial side of the intramedullary device.

15. A method comprising:
    providing an intramedullary device extending from a first end to a second end along a longitudinal axis, wherein each of the first and second ends is configured to be a driving end, wherein each of the first and second ends is configured to be a leading end, the intramedullary device including:
        a proximal region proximate the first end, a distal region proximate the second end, and a mid region positioned between the proximal region and the distal region,
        a first bore extending through the intramedullary device transverse to the longitudinal axis,
        a second bore extending through the intramedullary device from a first opening to a second opening, and a third bore extending through the intramedullary device from the first opening to a third opening, inserting the intramedullary device into a femur, wherein the intramedullary device is configured to be inserted:

from a distal end of the femur such that the first end is the leading end and the second end is the driving end, and from a proximal end of the femur such that the second end is the leading end and the first end is the driving end; and inserting a first fastener through the first bore to secure the intramedullary device within the femur.

16. The method of claim 15, further comprising:

inserting a second fastener through a fourth bore defined by the mid region of the intramedullary device.

17. The method of claim 15, further comprising:

inserting a second fastener through the second bore extending through the intramedullary nail transverse to the longitudinal axis, such that the second fastener extends from the first opening to the second opening.

18. An intramedullary device comprising:

a first end, a second end, and a first longitudinal axis extending from the first end to the second end, wherein the first end is configured to be a leading end and a driving end, wherein the second end is configured to be the leading end and the driving end;

a proximal region extending from the end;

a distal region extending from the second end; and a mid region positioned between the proximal region and the distal region, the mid region defining a first bore extending through the intramedullary device transverse to the longitudinal axis, wherein the intramedullary device is configured to be inserted into a femur in a proximal direction from a knee joint with the first end as the leading end and the second end as the driving end, wherein the intramedullary device is configured to be inserted into the femur in a distal direction from a hip joint with the second end as a leading end and the first end as a driving end.

19. The intramedullary device of claim 18, further comprising a second bore positioned at the mid region and extending through the intramedullary device transverse to the longitudinal axis.

20. The intramedullary device of claim 18, further comprising:

a second bore extending through the intramedullary device transverse to the longitudinal axis from a first opening to a second opening; and a third bore extending through the intramedullary device transverse to the longitudinal axis from the first opening to a third opening, wherein the second and third bores are positioned in the proximal region or the distal region.

* * * * *

UNITED STATES PATENT AND TRADEMARK OFFICE
CERTIFICATE OF CORRECTION

PATENT NO. : 10,456,177 B2
APPLICATION NO. : 15/837019
DATED : October 29, 2019
INVENTOR(S) : Sems et al.

Page 1 of 1

It is certified that error appears in the above-identified patent and that said Letters Patent is hereby corrected as shown below:

On the Title Page

On page 2, in Column 2, item (56), under "Other Publications", Line 27, delete "Feb." and insert --Mar.-- therefor On page 2, in Column 2, item (56), under "Other Publications", Line 34, delete "Applicaiton" and insert --Application-- therefor In the Claims In Column 9, Line 27, in Claim 18, after "from the", insert --first--

In Column 10, Lines 13-14, in Claim 19, delete "comprising" and insert --comprising:-- therefor Signed and Sealed this
Twenty-sixth Day of May, 2020

Andrei Iancu
*Director of the United States Patent and Trademark Office*